United States Patent [19]

Hanyu et al.

[11] 4,058,073
[45] Nov. 15, 1977

[54] CASE FOR PORTABLE SEWING MACHINES

[75] Inventors: Susumu Hanyu, Hachioji; Takashi Amano, Tokyo, both of Japan

[73] Assignee: Janome Sewing Machine Co. Ltd., Tokyo, Japan

[21] Appl. No.: 726,421

[22] Filed: Sept. 24, 1976

Related U.S. Application Data

[63] Continuation of Ser. No. 610,407, Sept. 4, 1975, Pat. No. 4,037,549.

[30] Foreign Application Priority Data

Sept. 10, 1974   Japan .............................. 49-108150

[51] Int. Cl.$^2$ ........................................... D05B 75/00
[52] U.S. Cl. ..................................... 112/258; 312/244
[58] Field of Search ................... 112/258, 217.1, 260; 312/244, 208; 248/20

[56] References Cited

U.S. PATENT DOCUMENTS

| | | | |
|---|---|---|---|
| 2,946,302 | 7/1960 | Krasnitz | 112/258 |
| 3,145,675 | 8/1964 | Momberg et al. | 112/258 |
| 3,162,406 | 12/1964 | Stanton et al. | 248/20 |
| 3,745,952 | 7/1973 | Giesselman | 112/258 |

FOREIGN PATENT DOCUMENTS 6,704,437   9/1968   Netherlands .......................... 112/258

Primary Examiner—George H. Krizmanich
Attorney, Agent, or Firm—Michael J. Striker

[57] ABSTRACT

A compact and lightweight case for a portable sewing machine has a hollow rectangular base which receives and is secured to the bed of a sewing machine and a cover which rests on the base and surrounds those parts of the machine which extend above the bed. One of such parts has a handle which extends outwardly through an opening in the top wall of the cover so that the case can be lifted through the medium of the sewing machine by lifting the machine by way of the handle.

7 Claims, 6 Drawing Figures

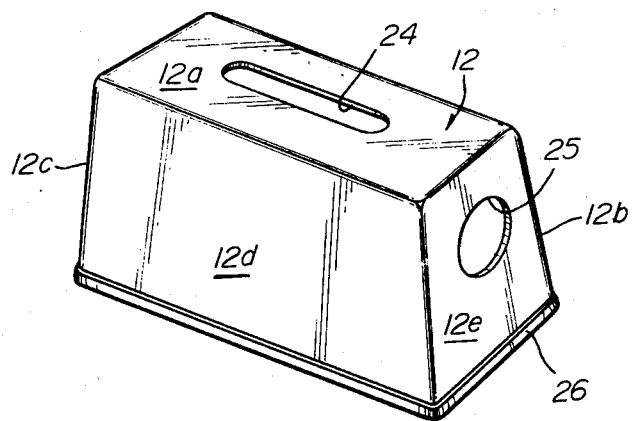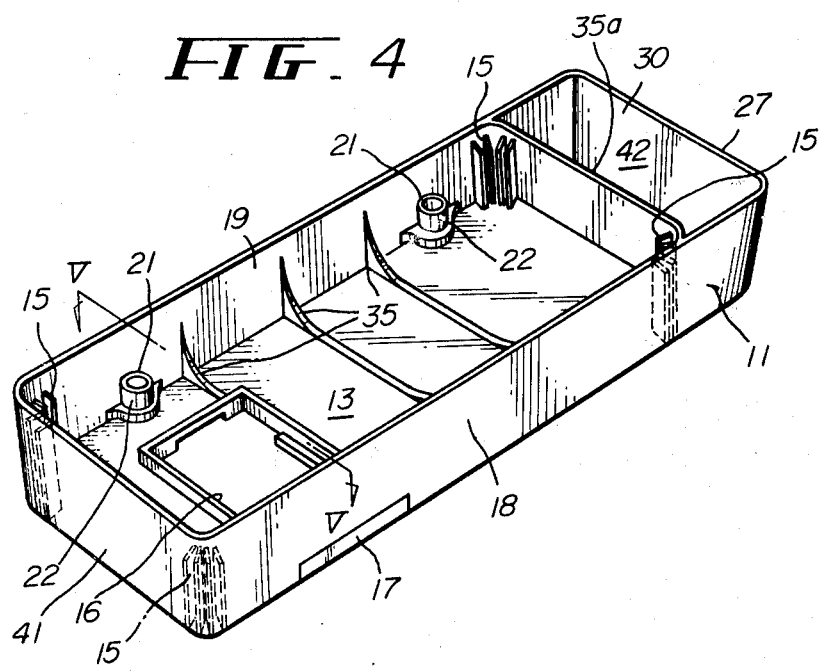

CASE FOR PORTABLE SEWING MACHINES

This application is a continuation of copending application Ser. No. 610,407, filed Sept. 4, 1975, now U.S. Pat. No. 4,037,549.

BACKGROUND OF THE INVENTION

The present invention relates to improvements in cases or receptacles for portable sewing machines.

A drawback of presently known cases for portable sewing machines is that they are heavy, unwieldy and expensive. This is due to the fact that a conventional case must be strong enough to support a confined sewing machine. As a rule, the bed of a portable sewing machine is secured to the base of a conventional case, and such conventional case further comprises a cover which is secured to the base by one or more hinges and has a handle by means of which the case (with a sewing machine confined therein) can be lifted when the cover is latched to the base. The material of the base of a conventional case must be strong and rigid enough to support the weight of the sewing machine, and the same applies for the cover since the machine is lifted through the medium of the cover and base. Moreover the hinge and hinges as well as the latch or latches for the cover must be strong and reliable since they carry the weight of the base plus the weight of the sewing machine when the cover is lifted by means of the handle. The manner in which the cover is hingedly secured to the base of a conventional case is similar to or identical with the manner of hingedly connecting the bed of a sewing machine to the top of a machine table.

SUMMARY OF THE INVENTION

An object of the invention is to provide a case for portable sewing machines whose weight, bulk and cost are but a small fraction of the weight, bulk and cost of a conventional case.

Another object of the invention is to provide a case which can be used in connection with existing portable sewing machines.

A further object of the invention is to provide a case which need not support the weight of a portable sewing machine when the latter is confined in the improved case and is being transported or transferred between different locations.

An additional object of the invention is to provide a case which can be rapidly and conveniently assembled with or detached from a portable sewing machine, which can fully conceal and shield all sensitive parts of the machine, which affords access to certain parts of the machine even if it is not completely detached from the machine, and wherein the cover need not be hinged and/or latched to the base.

Still another object of the invention is to provide a lightweight case whose cover may but need not consist of self-supporting material and whose sections may be mass-produced at a fraction of the cost of heretofore known cases for portable sewing machines.

The invention is embodied in a case for a portable sewing machine of the type having a normally rectangular work supporting bed, parts mounted on and extending above the bed, and a handle mounted on the parts. For example, the handle can be mounted on top of a hollow bracket which is secured to the top of a column opposite a flywheel and carries a hollow head for the needle bar mechanism. The case comprises a hollow base having an open top and serving to receive the bed of a portable sewing machine whereby the bed preferably rests on supporting elements mounted in the interior of the base at the corners of a preferably polygonal bottom wall of the base, threaded fasteners or analogous means for separably securing the base to the bed of a portable sewing machine in the case, and a cover which at least partially surrounds the parts on the bed of the machine in the case. The cover has a preferably elongated opening through which the handle extends outwardly so that the case can be lifted through the medium of the machine therein by lifting the machine by way of the handle.

In addition to the aforementioned polygonal (preferably rectangular) bottom wall, the base preferably comprises four side walls which extend upwardly from the bottom wall. The cover preferably comprises a top wall which is formed with the aforementioned opening for the handle and side walls extending downwardly from the top wall. One side wall of the cover may be formed with a preferably circular second opening for a portion of or the entire flywheel. The marginal portion of the base (such marginal portion surrounds the open top of the base) preferably serves as a means for supporting the marginal portion surrounding the open lower end of the cover.

The novel features which are considered as characteristic of the invention are set forth in particular in the appended claims. The improved case itself, however, both as to its construction and the mode of assembling the same, together with additional features and advantages thereof, will be best understood upon perusal of the following detailed description of certain specific embodiments with reference to the accompanying drawing.

BRIEF DESCRIPTION OF THE DRAWING

FIG. 3 is a perspective view of the cover;

FIG. 4 is an enlarged perspective view of the base;

DESCRIPTION OF THE PREFERRED EMBODIMENT

Figure 1:
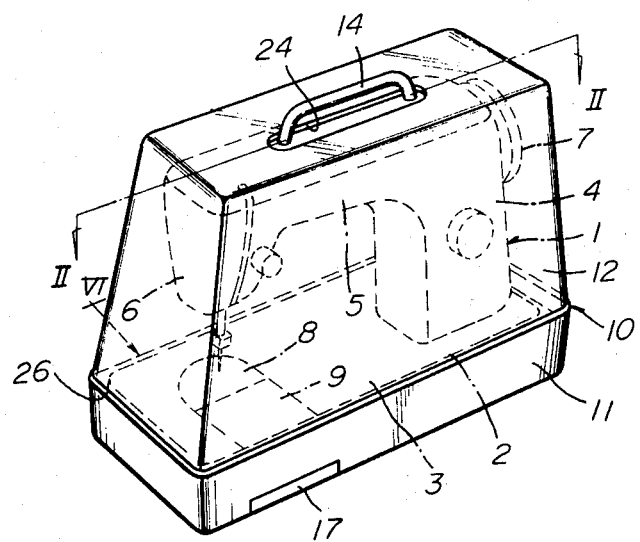
FIG. 1 is a perspective view of a case which embodies the invention, the sewing machine in the case being indicated by broken lines save for the handle which extends upwardly through the opening in the top wall of the cover.
Figure 2:
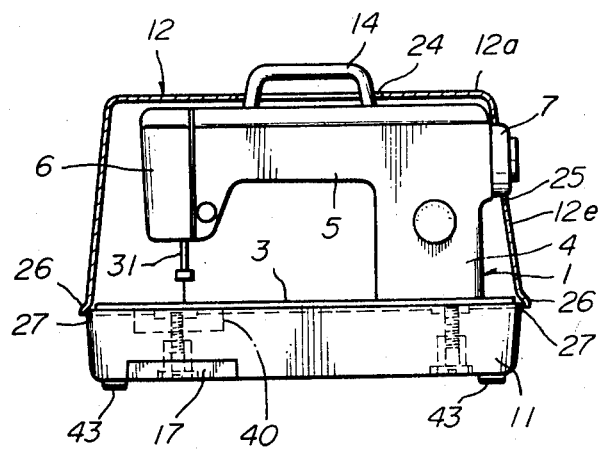
FIG. 2 is a front elevational view of the case with the cover shown in vertical section taken along the line II—II of FIG. 1.

Referring first to FIGS. 1 and 2, there is shown a case 10 which serves to confine a portable sewing machine 1. The sewing machine comprises a hollow rectangular bed 2 having at its upper side a work supporting surface 3. The bed 2 supports several parts including an upwardly extending hollow upright or standard 4 carrying an overhanging hollow bracket 5 which is spaced apart from the bed 2 and the free end portion of which constitutes a hollow head 6 for a needle bar mechanism 31. The upper end portion of the standard 4 supports a flywheel 7 which is adjacent the bracket 5, and the bed 2 carries a throat plate 8 and a slide plate 9 with the former disposed below the needle bar mechanism 31. The top portion of the bracket 5 supports or is made integral with an elongated inverted U-shaped handle 14 which extends upwardly through an elongated opening 24 in the top wall 12a of a cover 12 constituting the detachable upper section of the improved case 10. One of the four side walls 12b, 12c, 12e of the cover 12 has a circular opening 25 for a portion of the flywheel 7. A loop taker mechanism 40 is mounted at the underside of the bed 2 below the slide plate 9 so that is accessible from above by shifting the plate 9 away from the plate 8.

Figure 5:
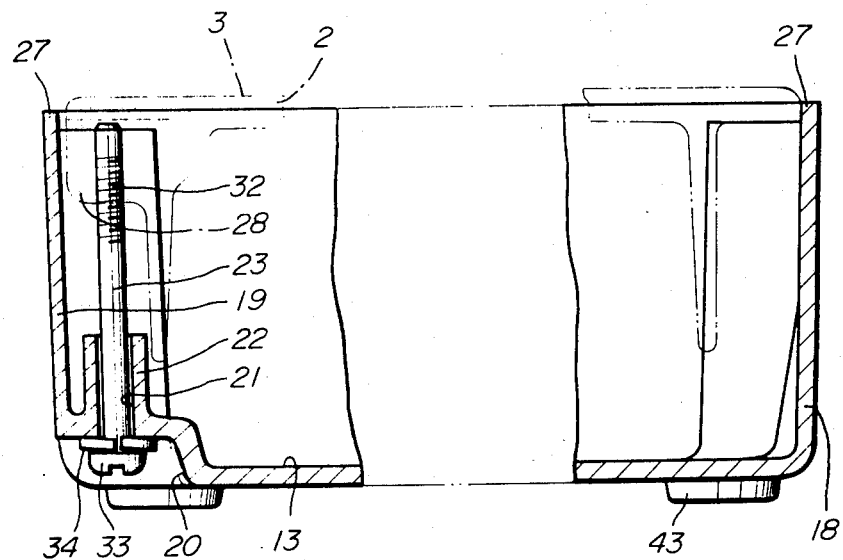
FIG. 5 is an enlarged transverse vertical sectional view taken along the line V—V of FIG. 4.

The manner in which a hollow rectangular base 11 of the improved case 10 is detachably secured to the bed 2 is shown in FIGS. 2, 4 and 5. The base 11 has a rectangular bottom wall 13 and four upwardly extending side walls including a front wall 18, a rear wall 19 and two lateral walls 41, 42. The bottom wall 13 has two upright cylindrical sleeves 22 with holes 21 for bolts 23 or analogous threaded fasteners. The sleeves 22 are adjacent to the rear wall 19 and register with bosses 28 at the underside of the bed 2. The bosses 28 have tapped bores 32 for the upper end portions of the bolts 23. The heads 33 of the bolts 23 abut against springy washers 34 and are received in suitable recesses 20 at the underside of the bottom wall 13.

Figure 6:
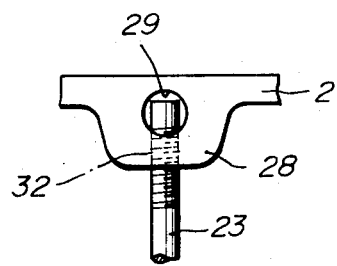
FIG. 6 shows a detail substantially as seen in the direction of arrow VI in FIG. 1.

As shown in FIG. 6, the bosses 28 of the bed 2 have horizontal holes 29 which intersect the respective tapped bores 32 and can receive portions of a hinge (not shown) provided in a conventional case or on a conventional machine table (not shown) in or on which the sewing machine 1 can be mounted upon detachment of the base 11 from the bed 2. The open ends of the holes 29 are located at the rear side of the bed 2. The means for supporting the bed 2 in the base 11 comprises four sets of suitable supporting elements 15 which are located in the interior of the base adjacent the four corners of the bottom wall 13.

The bottom wall 13 of the base 11 has a rectangular window 16 which is located below and in register with the loop taker mechanism 40 when the bed 2 is properly mounted in the base 11. The window 16 may be exposed or closed by a closure 17 which is slidably mounted in the bottom wall 13 and is movable between a first or extended position in which the window 16 is exposed so that the operator can gain access to the mechanism 40 and a second position (shown in FIG. 4) in which the closure prevents entry of dust or other foreign matter into the base 11.

The base 11 defines a compartment 30 which is located to the right of the two right-hand supporting elements 15 of FIG. 4 and is accessible from above when the cover 12 is lifted. The compartment 30 can serve for storage of sewing accessories, not shown. The base 11 further comprises reinforcing ribs 35 and 35a which extend transversely of the bottom wall 13 between the side walls 18 and 19. The reinforcing rib 35a is higher than the ribs 35 and constitutes a partition between the compartment 30 and the major part of the interior of the base 11.

The side walls 12b–12e of the cover 12 preferably diverge downwardly toward the outwardly flaring marginal portion or flange 27 of the base 11. The lowermost parts of the walls 12b–12e preferably constitute a second marginal portion or flange, indicated at 26, which rests on the flange 27 when the cover 12 assumes the position shown in FIGS. 1 and 2. In such position of the cover 12, the improved case practically completely confines the machine 1.

An important advantage of the improved case is that it can properly shield a portable sewing machine even if its sections 11 and 12 (and especially the cover 12) consist of lightweight material and even if the walls of the cover 12 are so thin that they would be unable to withstand stresses which would arise if the machine were to be lifted by way of the cover. This is achieved by providing the cover with the opening 24 so that a person wishing to transport the sewing machine 1 in the case 11–12 can lift the machine by way of the handle 14 whereby the machine automatically lifts the case because the base 11 is secured to the bed 2 by fasteners 23 and the marginal portion 26 of the cover 12 rests on the marginal portion 27 of the base. All that counts is to insure that the base 11 can stand the weight of the sewing machine 1 when the bed 2 is inserted into and rests on the supporting elements 15 of the base and the legs 43 of the base rest on a supporting surface.

Another important advantage of the improved case is that the cover 12 need not (even though it may) be locked or coupled to the base 11. This is due to the fact that the cover 12 is properly oriented with respect to and adequately supported by the base when the handle 14 extends upwardly through the opening 24, when the flywheel 7 extends (at least in part) outwardly through the opening 25, and when the marginal portion 26 rests on the marginal portion 27.

A further important advantage of the improved case is that it occupies little room. The compactness of the case is attributed to the fact that a portion of the flywheel 7 can extend from the cover 12 and that the depth of the base 11 need not appreciably exceed the thickness of the bed 2 plus the mechanism 40 therebelow. The downwardly diverging side walls 12b–12e of the cover 12 also contribute to compactness of the case, as well as the fact that the handle 14 can extend from the cover at all times.

The improved case can be made of a variety of materials (such as a metal or a synthetic plastic substance) at a cost which is a small fraction of the cost of conventional cases for portable sewing machines. This will be readily appreciated since the cover 12 need not even be self-supporting, i.e., it can be made of flexible plastic material as long as it exhibits an opening 24 for the handle 14 and a reasonably rigid marginal portion 26 so that it can rest on the base 11 in an optimum position. Also, the case need not be provided with latches or other means for coupling the base to the cover in a manner known from conventional cases wherein the cover and the coupling means must be strong enough to insure that the cover does not open and is not deformed when its handle is lifted in order to lift the sewing machine in the interior of such conventional case. The absence of coupling means further contributes to compactness of the improved case.

Without further analysis, the foregoing will so fully reveal the gist of the present invention that others can, by applying current knowledge, readily adapt it for various applications without omitting features which fairly constitute essential characteristics of the generic and the specific aspects of our contributions to the art and, therefore, such adaptations should and are intended to be comprehended within the meaning and range of equivalence of the claims.

What is claimed as new and desired to be protected by Letters Patent is set forth in the appended claims:

1. A case for a portable sewing machine of the type having a work supporting rectangular bed, a standard secured to said bed, a bracket secured to said standard and spaced from said bed, a flywheel mounted on said standard adjacent to said bracket, and a handle mounted on the top of said bracket, comprising a hollow base having an open top defined by an upper marginal portion and being arranged to receive said bed of the sewing machine, said base being rectangular and having a bottom wall and four side walls extending upwardly from said bottom wall; a separate cover having a top wall and four side walls extending downwardly from said top wall said cover having an opening provided in said top wall through which said handle of the sewing machine, whose bed is supported by said base, extends so that said case can be lifted through the medium of the machine by way of said handle, said cover having a second opening through which said flywheel of the sewing machine extends, said cover further having a lower open end defined by a lower marginal portion abutting against said upper marginal portion of said base without being fastened thereto; and means securing said base to said bed.

2. A case for a portable sewing machine of the type having a work supporting bed, a standard secured to said bed, a bracket secured to said standard and spaced from said bed, a flywheel mounted on said standard adjacent to said bracket, and a handle mounted on the top of said bracket, comprising a hollow base having an open top defined by an upper marginal portion and being arranged to receive said bed of the sewing machine; a separate cover having an elongated opening through which said handle of the sewing machine, whose bed is supported by said base, extends so that said case can be lifted through the medium of the machine by way of said handle, said cover having a second substantially circular opening through which said flywheel of the sewing machine extends, said cover further having a lower open end defined by a lower marginal portion abutting against said upper marginal portion of said base without being fastened thereto; and means securing said base to said bed.

3. A case for a portable sewing machine of the type having a work supporting bed, a standard secured to said bed, a bracket secured to said standard and spaced from said bed, a flywheel mounted on said standard adjacent to said bracket, and a handle mounted on the top of said bracket, comprising a hollow base having an open top defined by an upper marginal portion and being arranged to receive said bed of the sewing machine; a separate cover having an opening through which said handle of the sewing machine, whose bed is supported by said base, extends so that said case can be lifted through the medium of the machine by way of said handle, said cover having a second opening through which said flywheel of the sewing machine extends, said cover further having a lower open end defined by a lower marginal portion abutting against said upper marginal portion of said base without being fastened thereto; and means securing said base to said bed comprising a plurality of threaded fasteners.

4. A case for a portable sewing machine of the type having a work supporting bed, a standard secured to said bed, a bracket secured to said standard and spaced from said bed, a flywheel mounted on said standard adjacent to said bracket, and a handle mounted on the top pf said bracket, comprising a hollow base having an open top defined by an upper marginal portion and being arranged to receive said bed of the sewing machine, said bed having a polygonal bottom wall and side walls extending upwardly from said bottom wall; means for supporting the bed of a machine in said case including supporting elements located in said base adjacent to the corners of said bottom wall; a separate cover having an opening through which said handle of the sewing machine, whose bed is supported by said base, extends so that said case can be lifted through the medium of the machine by way of said handle, said cover having a second opening through which said flywheel of the sewing machine extends, said cover further having a lower open end defined by a lower marginal portion abutting against said upper marginal portion of said base without being fastened thereto; and means securing said base to said bed.

5. A case for a portable sewing machine of the type having a work supporting bed, a standard secured to said bed, a bracket secured to said standard and spaced from said bed, a flywheel mounted on said standard adjacent to said bracket a mechanism is mounted at the underside of said bed, and a handle mounted on the top of said bracket, comprising a hollow base having an open top defined by an upper marginal portion and being arranged to receive said bed of the sewing machine, said base including a bottom wall having a window in register with the mechanism at the underside of the bed of the machine in said case; a separate cover having an opening through which said handle of the sewing machine, whose bed is supported by said base, extends so that said case can be lifted through the medium of the machine by way of said handle, said cover having a second opening through which said flywheel of the sewing machine extends, said cover further having a lower open end defined by a lower marginal portion abutting against said upper marginal portion of said base without being fastened thereto; and means securing said base to said bed.

6. A case as defined in claim 5, wherein said base further comprises a closure for said window, said closure being movable with respect to said bottom wall between first and second positions in which said window is respectively exposed and closed.

7. A case for a portable sewing machine of the type having a work supporting bed, a standard secured to said bed, a bracket secured to said standard and spaced from said bed, a flywheel mounted on said standard adjacent to said bracket, and a handle mounted on the top of said bracket, comprising a hollow base having an open top defined by an upper marginal portion and being arranged to receive said bed of the sewing machine, said base having a compartment laterally adjacent to the bed of the sewing machine in said case; a separate cover having an opening through which said handle of the sewing machine, whose bed is supported by said base, extends so that said case can be lifted through the medium of the machine by way of said handle, said compartment of said base being open at the top and being accessible upon lifting of said cover, said cover having a second opening through which said flywheel of the sewing machine extends, said cover further having a lower open end defined by a lower marginal portion abutting against said upper marginal portion of said base without being fastened thereto; and means securing said base to said bed.

* * * * *